United States Patent [19]

Wallach

[11] Patent Number: 4,959,341

[45] Date of Patent: Sep. 25, 1990

[54] BIODEGRADABLE SUPERABSORBING SPONGE

[75] Inventor: Donald F. H. Wallach, Brookline, Mass.

[73] Assignee: Micro Vesicular Systems, Inc., Nashua, N.H.

[21] Appl. No.: 320,944

[22] Filed: Mar. 9, 1989

[51] Int. Cl.$^5$ .................. B01J 13/00; B01J 20/22; B01J 20/26

[52] U.S. Cl. ..................... 502/404; 134/40; 134/41; 134/42; 210/660; 210/767; 252/194; 252/315.3; 604/368

[58] Field of Search ............. 502/404; 252/194, 315.3; 604/368

[56] References Cited

U.S. PATENT DOCUMENTS

| | | | |
|---|---|---|---|
| 3,969,280 | 7/1976 | Sayce et al. | 252/522 |
| 4,090,013 | 5/1978 | Ganslaw et al. | 526/15 |
| 4,160,063 | 7/1979 | Titus | 428/389 |
| 4,454,055 | 6/1984 | Richman et al. | 252/194 |
| 4,486,335 | 12/1984 | Majewicz | 252/315.3 |
| 4,548,847 | 10/1985 | Aberson et al. | 252/194 X |
| 4,610,678 | 9/1986 | Weisman et al. | 604/368 |
| 4,786,415 | 11/1988 | Shibata et al. | 502/404 X |
| 4,812,486 | 3/1989 | Hosokawa et al. | 502/404 X |
| 4,826,880 | 5/1989 | Lesniak et al. | 521/53 |

FOREIGN PATENT DOCUMENTS 1152483 8/1983 Canada .................. 502/404

Primary Examiner—Patrick P. Garvin
Attorney, Agent, or Firm—Lahive & Cockfield

[57] ABSTRACT

A new superabsorber which gels and cross-links as hydrated has been developed. The superabsorber contains a branched-chain polyanionic carbohydrate such as carboxymethylcellulose, a cross-linking agent, and a hydrophobic carboxylic acid. The superabsorber is biodegradable and non-toxic.

14 Claims, No Drawings

BIODEGRADABLE SUPERABSORBING SPONGE

BACKGROUND OF THE INVENTION

The present invention relates to biodegradable gels which act as superabsorbing sponges. More particularly, the gel of the invention has as high, or higher, liquid and saline uptake than the polyacrylate superabsorbers now being used while having the advantage of being completely biodegradable.

Biodegradability has become a necessity in society in the last few years. As more and more products are made disposable, the waste problems associated with these disposables have become increasingly important. One example of this is the disposable diaper field. Until a few years ago, disposable diapers, though convenient, had not received widespread use because the amount of liquid which could be absorbed was limited. This limitation lead to use of the diapers for extraordinary circumstances but they were not feasible for most people on a day-to-day basis because of the leakage and resulting diaper rash problem. In order to solve these problems, the diaper manufacturers first used very thick diapers, placing large amounts of fiber such as cellulose in the diaper to act as a liquid, primarily saline and urine, absorber. These bulky diapers still had limitations on the amount of liquids they could retain while the bulk made them uncomfortable for the infants to wear.

The first major improvement in the disposable diaper field was the addition of the so-called "superabsorbers" as liquid traps. These superabsorbers are primarily polyacrylate particles which are placed in the diaper in loose form or are entrapped among cellulose fibers. These polyacrylate particles absorb large quantities of water by swelling and acting as individual pseudo-sponges. Since the amount of saline and urine which can be absorbed by these superabsorbers is so much greater than cellulose or other natural fibers, very thin diapers could be used, minimizing the problems to infants and making disposables the diaper of choice. The polyacrylate gel beads move freely relative to each other and form large spaces between each other. However, once fully hydrated, these polyacrylate superabsorbers tend to clump, causing a lumpy diaper and discomfort to the infant.

In addition to the use in diapers, the superabsorbers have other uses. Many other items which are used for absorption of liquid are a fertile ground for use of the superabsorbers. However, the polyacrylate superabsorbers have one major disadvantage; they are not biodegradable. This means that the diapers and all other products made using these superabsorbers are not degraded for decades; in fact, they need hundreds of years to breakdown. This leads to the aforementioned waste problem. Another disadvantage of the polyacrylates is that they absorb maximally at 0% saline while urine and most body fluids are about 0.15 N saline.

Materials which absorb liquid and are biodegradable such as those of the present invention have other possible uses as well. The entrapment of particles, including macromolecules such as hemoglobin and cells such as erythrocytes, is particularly important for feminine napkins and similar products. Superabsorbers have not made a great dent in this field even though they have the necessary liquid absorption because they cannot entrap large particulates.

Another possible use for a biodegradable material which will entrap liquid and/or particles is as a sustained release vehicle. In certain instances, the molecules to be delivered can be part of the structural material of the sponge itself. Most materials which are presently being tested as sustained release vehicles, e.g., microcapsules, liposomes and related capsular type products, have substantial costs and time associated with their manufacture. The ability to make a product in situ, apply it to a given area, and then let it degrade under ordinary conditions to release entrapped material, would solve many problems.

A further use of a gel which entraps liquids and particles is as a biological protective barrier. For example, a gel which entraps bacteria as it is hydrated, or prevents their passage once formed, can be used as a wound dressing, protecting the wound from bacteria while allowing air flow and/or free flow of liquid to the injury. A further use is in a diaper where coliform bacteria can breakdown urea in urine to ammonia, changing the pH and promoting diaper rash.

Accordingly, an object of the invention is to provide a biodegradable material that has high uptake for water and saline.

Another object of the invention is to provide a biodegradable carrier or sustained release delivery system for drugs and other molecules.

A further object of the invention is to provide a material and method for entrapment of particulates such as erythrocytes and protein molecules such as hemoglobin.

A still further object of the invention is to provide a protective barrier which prevents the passage of particles such as bacteria or macromolecules, e.g., for use as a wound bandage.

These and other objects and features of the invention will be apparent from the following description.

SUMMARY OF THE INVENTION

The present invention features a composition of matter which acts as a synthetic sponge as well as methods of absorbing aqueous or saline solutions. The invention further features methods of entrapping particles in a gel. The gel-like composition of matter can be used as a protective barrier and as a sustained release vehicle which releases entrapped particles or molecules such as drugs over time.

In brief, a composition of matter has been developed which acts as a synthetic sponge when allowed to hydrate. A high molecular weight, complex carbohydrate with multiple anion-terminated branches and a cross-linking agent are blended under substantially anhydrous conditions, preferably with a carboxylic acid with a substantial hydrophobic region. Preferred carboxylic acids with substantial hydrophobic regions are fatty acids selected from a group consisting of lauric acid, palmitic acid, oleic acid, stearic acid, benzoic acid, or mixtures thereof. A substantial hydrophobic region means and implies a region with a substantial hydrocarbon chain or ring structure. Preferred branch complex carbohydrates include carboxymethylcellulose, and chemical analogues thereof. Linear complex carbohydrates such as cellulose, gum xanthan, gum karaya, or alginic acid may also be included.

Once the components are intimately blended, e.g., milled together, the components of the mixture can be hydrated and cross-linked substantially simultaneously when in the presence of the hydrating solution. Any of the components may be premixed together or impregnated with one another. In addition, the other reactants may be derivatized with the complex or linear carbohydrates using an isopropoxide or other similar reaction. Some or all of the fatty acid can be replaced with a "functional fatty acid" or a long-chain carboxylic acid. As used herein, the term "functional fatty acid" means, includes and defines a molecule having a terminal carboxylic acid, a substantial aliphatic portion, and a biological function other than as a breakdown product or precursor in the food chain. Functional fatty acids include acids such as undecylenic acid, arachidonic acid, prostaglandins, prostacyclins, thromboxanes, and their derivatives, chemical analogues and precursors.

As noted, the composition of matter of the invention includes a cross-linking agent as an essential component. The preferred cross-linking agents are metallo-organic compounds of multivalent metals. Organic cross-linking agents such as chitosan, Poly-Cup, chymene, and jeffamine may be used, but are less efficient than the metallo-organic complexes. Oxytetracyline is a highly effective cross-linking agent but has limited application because of its biological activity. Although bivalent molecules such as calcium might be used in certain circumstances, the multivalent metals (valence 3 and over) such as aluminum or chromium are preferred. For many applications aluminum in the form of hydroxy-aluminum diacetate, borate-stabilized dihydroxy-aluminum acetate and/or aluminum sulfate/citrate, may be satisfactory. A most preferred cross-linking agent providing superior performance is an aluminum metallo-organic complex of the hydroxy-aluminum/hydrophobic carboxylate form Such as hydrOxy-aluminum benzoate. This agent can act as both the hydrophobic carboxylic acid and the cross-linking agent in a single molecule. Other hydrophobic carboxylic acids such as laurate, stearate, oleate or benzoate can also be used in the metallo-organic complex.

The invention further features a method of absorbing aqueous or saline solutions using the biodegradable synthetic sponge composition of the invention. The synthetic sponge composition is provided in a substantially unhydrated form, for example, by blending the components together to obtain particles of the desired size, and then the solution is absorbed by contacting the solution with the synthetic sponge composition. The synthetic sporige composition hydrates to absorb the solution and substantially simultaneously cross-links into a gel which binds the solution.

The same basic material may be used to encapsulate particles in a gel. The synthetic sponge composition is provided in a substantially unhydrated form and a solution containing the particles to be entrapped within the gel is mixed with the composition. The gel forms by cross-linking, absorbing the liquid and entrapping the particles within the gel. Particles which can be entrapped in this way include macromolecules or proteins such hemoglobin, bacteria, or cells such as erythrocytes.

Substantially the same entrapment procedure can be used to create a sustained release vehicle. For example, gels cross-linked by oxytetracycline can be used as a sustained release vehicle for this drug. Many positively charged drugs can be held in polyanionic gels for sustained release. By modifying the ratios of the different components, and selecting the specific materials which make up the gel, the stability, absorption levels, and firmness of the gel can be modified. For example, changing the fatty acid/carbohydrate ratio can dramatically change the absorption, and the subsequent release rate, of liquid from the gel. Further, the addition of other materials to the gel, e.g., surfactants such as polyoxyethylene fatty acid ethers or spacers such as silica or clays, can change the properties of the gel. This change of properties is more clearly explained in the description and the Examples.

DETAILED DESCRIPTION OF THE INVENTION

The hydrated gel described herein is formed by the simultaneous hydration and cross-linking by a cross-linking agent of polyanionic carbohydrates, preferably together with hydrophobic carboxylates. In contrast to the polyacrylate superabsorbers, which necessarily form discrete particles (as do covalently cross-linked molecules such as cross-linked carboxymethylcellulose, gelatins, and alginates), the material of the present invention exists in uncross-linked form prior to hydration. Upon hydration, the material forms extend, water-binding networks of biodegradable carbohydrate polymer, preferably further cross-linked with extended multilamellar sheets of degradable, anionic lipid. Macroscopically, the gels are stable and can extend several centimeters in several directions upon hydration. These gels can also be formed into a variety of geometries such as rods, disks, and slabs. The consistency of the gel, and the amount of liquid absorbed, can be changed by modifying the initial composition. In addition, a partially hydrated gel can be further hydrated at a later time by absorption of more liquid.

The capacity for uptake of liquid of the compositions of the present invention furthermore depends on the ratio of active acid, e.g., lipids, to active carbohydrate. At low lipid/carbohydrate ratios (on a weight basis), e.g., a 0.1–0.2 ratio, high fluid absorption is observed. In fact, as may be seen from the following Examples, the uptake of 0.15 N saline is considerably greater than that of the polyacrylate superabsorbers. When the ratio of fatty acid to carbohydrate is much higher, e.g., approximately 1, the gels do not absorb as much liquid, give up the liquid easier, and act as better delivery systems.

Functional fatty acids can be used to replace some or all of the fatty acid. The major advantage of using these functional fatty acids is that as the gels are degraded, the functional fatty acid is released. This acts as a type of delivery system which can have a much higher concentration of the material to be delivered than could be possible in another type of encapsulation or entrapment system. In fact, a certain proportion of the fatty acid can be replaced by any carboxyl terminated molecule.

Although branched complex carbohydrates are necessary for practice of the invention, some of these branched carbohydrate fractions can be replaced by linear carbohydrates such as cellulose. The addition of these linear carbohydrates appears to improve the absorption capability of the system, acting synergistically with the other components. Other linear carbohydrates which have been shown to be effective include carbohydrates with terminal glucoronic acid such as alginic acid, gum xanthan and gum karaya. Non-cross-linkable soluble carboxylic acids do not appear to work.

The following Examples will more clearly explain the procedures and processes of the present invention.

EXAMPLE 1

This Example shows the fluid uptake of saline for a composition of the invention with low lipid/carbohydrate ratio under pressure conditions designed for testing polyacrylate superabsorbers. Approximately 0.05 g (0.2 mmol) of palmitic acid was blended with 0.5 g carboxymethylcellulose and 0.02 g (0.14 mmol) borate-stabilized dihydroxy aluminum acetate and 1.5 g of cellulose fiber. Blending took place at room temperature by mixing the materials together until they were uniformly blended. The materials were then milled into 500 micron particles.

In a parallel experiment, a high lipid/carbohydrate material was made and tested under the same conditions. This high ratio material is made by blending 1 g of palmitic acid with 1 g of carboxymethylcellulose and 0.04 g of the borate-stabilized dihydroxy aluminum acetate complex. Small portions of the sample (approximately 0.1 g) were blended with 0.5 g of cellulose fiber.

The two samples were tested under the same procedure, as was a polyacrylate superabsorber. The test procedure hydrated the materials by capillary action with 0.15 M NaCl under applied load of 0.22 lbs./in$^2$ for sixty minutes at room temperature. The amount of fluid take up was then determined gravimetrically. The data shown in all the Tables of Examples show the amount of fluid uptake for the synthetic sponge, determined by correcting for the amount of fluid taken up by the cellulose alone which was determined separately.

TABLE 1

| System | Fluid Uptake (ml/g) |
| --- | --- |
| Low Lipid/Carbohydrate | 37.3 |
| High Lipid/Carbohydrate | 21.1 |
| Superabsorber | 30.4 |

Table 1 shows that the fluid uptake for the low lipid/-carbohydrate ratio, in ml of liquid/g of absorber, is higher than the superabsorber while a lower amount, but still significant, is absorbed by the high lipid/carbohydrate ratio material. This shows that a simple modification of ratios, using exactly the same materials, can lead to a control in the amount of liquid taken up by the gel.

EXAMPLE 2

In this Example, a different test was used to determine fluid retention by two different gels of the invention and a polyacrylate superabsorber. The first gel, a low lipid/carbohydrate ratio gel, was made by blending 0.05 g palmitic acid with 0.5 g carboxymethylcellulose and 0.02 g of the borate-stabilized dihydroxy aluminum acetate complex. Approximately 0.3 g of this mixture was then blended with 1.5 g of cellulose fiber.

The second gel of the invention was made by blending 1.0 g of palmitic acid with 1.0 g of carboxymethylcellulose and 0.04 g of the borate-stabilized dihydroxy aluminum acetate complex. Again, 0.3 g of this mixture was blended with 0.5 g of cellulose fiber.

Samples of each of the two compositions of the invention and a superabsorber (0.3 g each) were sealed in tea bags and immersed in 0.15 N saline for thirty minutes at room temperature. After removal from the saline, the tea bags were centrifuged at 300 X g for thirty minutes and the amount of saline retained within the material was determined gravimetrically. Again, there was a correction made for the excess cellulose. Table 2 shows the results of this testing.

TABLE 2

| System | Fluid Retention (ml/g) |
| --- | --- |
| Low Lipid/Carbohydrate | 43.0 |
| High Lipid/Carbohydrate | 21.1 |
| Superabsorber | 36.5 |

As is clear, the low lipid/carbohydrate ratio material had a greater fluid retention than the superabsorber while the high lipid/carbohydrate ratio material had a lower retention.

EXAMPLE 3

In this series of experiments, the retention of particulate material by the gels of the invention were tested. In each experiment, 1.0 g of palmitic acid was uniformly blended with 1.0 g of carboxymethylcellulose and 0.04 g of the borate-stabilized dihydroxy aluminum acetate complex, making a high ratio gel. About 0.5 g of the mixture was hydrated with 25 ml of the test suspension. In the first test, the hydration material was a suspension of human red cells in 0.15 N saline. The gelation occurred within thirty minutes. After two hours, the resulting gel was centrifugally washed with five volumes of 20% dextran (140,000 Mol. Wt.) dissolved in 0.15 N saline. Each wash had the sample centrifuged for thirty minutes at 3,000 rpm in a Beckman centrifuge. The red cell-containing gel contracted and floated to the top half of the centrifuge tube while there was substantially no release of red cells. If the cells had been free, they would pellet at the bottom of the centrifuge tube. This shows the retention of the particulate matter, in particular erythrocytes, by the gel of the invention. Over 99% of the cells were contained within the gel, as determined spectrophotometrically. This was true for red cell suspension of 2.5–12.5 times the mixture amount used. In a similar experiment with heparin-treated whole blood, the gel was able to absorb 20 times its weight with similar retention characteristics.

Similar experiments were carried out replacing the red cell suspension with a solution of human hemoglobin in normal saline. Gelation lead to complete incorporation of the hemoglobin solution. After standing for two days, the gel was centrifugally washed five times at the 3,000 rpm for thirty minutes in the Beckman centrifuge in a dextran gradient. Only traces of hemoglobin were observed released into the dextran barrier while substantially all of the rest of the hemoglobin was retained within the gel. By spectrophotographics measurement, about 88% of the hemoglobin was retained.

A further experiment was carried out using the same procedure but replacing the red cell suspension with a suspension of paucilamellar lipid vesicles, made using the materials and procedures described in U.S patent application Ser. No. 157,571 now U.S. Pat. No. 4,911,928, with an average diameter of about 0.5 $\mu$. These vesicles had an oil-based center with the liposoluble red dye "Oil Red 0" incorporated in the oil as a marker. Gelation in the presence of the vesicles lead to complete incorporation of the vesicles. Over two days, five centrifugal washings of the gels showed a gradual release of the dye-containing vesicles without fractionation or breakdown of the vesicles. This shows that this type of gel could be used as a sustained release vehicle, or that it can act as a protective barrier to large particles. Other paucilamellar lipid vesicles have also been encapsulated.

EXAMPLE 4

In this experiment, the same high lipid/carbohydrate ratio gel as used in Example 3 was used to show the effects of isotonic changes and permeability of small particles. The gel was manufactured as described above and was hydrated with 25 ml of plain water. The gel was then soaked alternately in several changes of 0.5 ml of 1 M sucrose then water.

The shifts from the hypertonic to hypotonic medium and back caused only transient changes in gel volume at the time of the change of the medium, indicating free permeability of the gels to sucrose. Therefore, it is expected that the gels would also be permeable to molecules of approximately the same size as sucrose including many drugs. Accordingly, the gels could be used as a wound bandage which allows passage of a drug through the gel to where it is necessary but protection against large particulate-type matter such as bacterial cells. In contrast, exposure of gels to a 20% solution of high molecular weight dextran (140,000 Mol. Wt.) causes reversible shrinking, suggesting that these molecules do not penetrate the gels and cause osmotic loss of water from the gels.

EXAMPLE 5

In this Example, a functional fatty acid, undecylenic acid, is used in place of a standard fatty acid in forming the gel of the invention. This functional fatty acid is a potent fungicide.

To make this gel, 1.0 g of undecylenic acid was uniformly blended with 1.0 g of carboxymethylcellulose and 0.036 g of the borate-stabilized aluminum acetate complex. The sample was hydrated by mixing 25 ml of water with 0.5 g of the mixture. Hydration was complete within thirty minutes, forming a soft gel. The gel slowly releases the undecylenic acid over time. A more rigid gel can be formed by using blends of the functional fatty acid with palmitic or stearic acid.

The soft gel is slightly turbid, spreads easily, and sticks to the skin. Because of this, a bandage or wound covering of the undecylenic acid gel could be applied to the skin, providing fungicidal benefits as well as protection against particulate bacteria and infection.

EXAMPLE 6

In this Example, two different metallo-organic complexes useful as cross-linking agents within the scope of the invention were made. The first, a palmitate-based aluminum metallo-organic complex (PX-L), is made by mixing 0.64 g palmitic acid (0.25 mmol) dissolved in 5 ml of ethanol with 1.4 g (10 mmol) aluminum monoacetate stabilized with boric acid in 5 ml of water. An opalescent solution resulted. This opalescent suspension can be mixed with carboxymethylcellulose (CMC), with or without cellulose fiber, to provide a cross-linking agent impregnated in the CMC. This same procedure may be used with equal molar amounts of lauric or stearic acid to form similar complexes.

To form an benzoate-based aluminum metallo-organic complex (BX-L), a more dilute solution is used. Specifically, 0.61 g of benzoic acid (0.50 mmol) was dissolved in 7.5 ml of ethanol. The benzoic acid solution was mixed with a solution containing 1.4 g (10 mmol) aluminum monoacetate stabilized with boric acid in 7.5 ml of water. Again, an opalescent suspension resulted. This cross-linking agent can also be impregnated into or derivatized with CMC or cellulose fiber.

EXAMPLE 7

In this Example, the organo-metallic cross-linking agents formed in Example 6 were used to form the sponge-like material of the invention. In the first such test, 0.2 g of carboxymethylcellulose (CMC), 0.04 g of palmitic acid (PA), 0.2 ml of the benzoate-based aluminum metallo-organic cross-linking agent (BX-L) made in Example 6, and 50 ml of 0.15 N saline were blended. As one of the two variations of the experiment, 0.6 g of cellulose was also used.

The mixture was hydrated by thirty seconds of magnetic stirring and the still-liquid mixture was transferred to 50 ml centrifuge tubes and centrifuged at 300 X g for thirty minutes. At the end of the thirty minute centrifuge period, any free fluid was collected by filtration through a 150 μ pore size nylon mesh. Highly cohesive, firm gels form within the thirty minute centrifugation.

Retention of liquid was measured at least twenty-four hours after formation. Gel piece aliquots were cut out, weighed, and placed in a centrifuge tube insert, closed its bottom by a perforated screen supporting a piece of non-woven tea-bag paper. After centrifugation at 300 X g for thirty minutes, the amount of liquid released from the gel was determined gravimetrically. Table 3 shows the results of this testing for the material of the invention (CMC/PA/BX-L), with or without cellulose. The same test was carried out using a similar amount of Sanwet IM1500 U.S., a polyacrylic superabsorber, as a control. All values with cellulose are corrected to non-cellulose activities in this and the following Examples.

TABLE 3

| System | Absorption (ml/g) |
|---|---|
| CMC/Palmitate/Benzoate X-link | 162 ± 10 |
| + Cellulose | 201 ± 4 |
| Polyacrylic Superabsorber | 60 ± 1 |
| + Cellulose | 70 ± 1 |

As can be seen from the results of Table 3, the composition of the invention, either with or without cellulose, clearly is superior to the polyacrylic superabsorbers in terms of retention of 0.15 N saline.

The identical experiment was performed using a composition of the invention which had the palmitate-based cross-linking agent (PX-L) in place of the benzoate-based cross-linking agent (BX-L). Table 4 shows the results of this experiment, again compared to the superabsorber results.

TABLE 4

| System | Absorption (ml/g) |
|---|---|
| CMC/Palmitate/Palmitate X-link | 207 ± 1 |
| + Cellulose | 205 ± 1 |
| Polyacrylic Superabsorber | 60 ± 1 |
| + Cellulose | 70 ± 1 |

EXAMPLE 8

In this Example, a 20% whole blood solution was tested for absorption by a composition of the invention made with the benzoate-based cross-linking agent (BX-L) of Example 6. The composition was made by mixing 0.2 g of carboxymethylcellulose, 0.04 g of palmitic acid, 50 ml of 20% whole blood, 0.15 N saline and 1 ml of the cross-linking agent. Again, the material was tested with and without 0.6 g of cellulose. After hydration, the still-liquid mix was divided into to two 25 ml portions, these were transferred to 50 ml centrifuge tubes, and gelation was allowed to proceed under centrifugation at 300 X g (average 4800 lbs./in$^2$) for thirty minutes. At the end of the centrifugation, any free fluid was collected by filtration though 150 μ pore size nylon mesh. Table 5 shows the results of this test. The value without the cellulose is equivalent to an absorption of 35 ml of whole blood, while the cellulose added value is even higher.

TABLE 5

| System | Absorption (ml/g) |
|---|---|
| CMC/Palmitate/Benzoate X-link | 175 ± 1 |
| + Cellulose | 223 ± 1 |

EXAMPLE 9

In this Example, undecylenic acid is incorporated into a gel containing the benzoate-based aluminum metallo-organic complex of Example 6. Approximately 0.5 ml of the cross-linking complex was combined with 0.5 ml carboxymethylcellulose and 0.5 g of undecylenic acid. The material was hydrated with 70 ml with deionized water. A high cohesive but mobile gel formed within thirty minutes. There was no release of water over a period of more than three hours and there was no separation of free undecylenic acid.

The same approach could be used to incorporate a variety of carboxyl terminal functional molecules such as prostaglandins, prostacyclins, thromboxanes and their precursors such as arachidonic acid. In addition, certain antibiotics such as oxytetracyline can be used in place of some or all of the cross-linking agents.

Other materials which could be used to replace part the fatty acid include carboxylic acids, carboxylic peptides, nonionic surfactants, and steroids such as cholesterol or hydrocortisone. Selection of proper acidic constituents can modify gel properties. The steroid can be present in the system up to at least 10% of the fatty acid without disturbing the gel. Therefore, these gels could be used as a delivery systems for a variety of molecules such as steroids.

In addition, as shown previously, lipid vesicles can be incorporated into the gels as particulate matter. Since these lipid vesicles can also be designed to carry a variety of materials which could not otherwise be carried in the gel, a wound patch or other covering made of the gel with the vesicles dispersed therein could be used to apply drugs on a time-released basis to a selected site.

Those skilled in the art will be able to determine other modifications of the exemplary procedures and materials. Such other modifications are within the scope of the following claims.

What is claimed is:

1. A composition of matter which acts as a synthetic sponge when allowed to hydrate comprising a non-hydrated mixture of:

a carboxylic acid with a substantial hydrophobic region;
   a branched complex carbohydrate; and
   a separate cross-linking agent;
   whereby said composition can be hydrated and cross-linked simultaneously in the presence of a hydrating solution.

2. The composition of claim 1 wherein said carboxylic acid comprises a fatty acid.

3. The composition of claim 2 wherein said fatty acid is selected from the group consisting of lauric acid, palmitic acid, stearic acid, oleic acid, and mixtures thereof.

4. The composition of claim 1 wherein said carboxylic acid comprises a functional fatty acid.

5. The composition of claim 4 wherein said functional fatty acid is selected from the group consisting of arachidonic acid, prostaglandins, prostacyclins and thromboxanes.

6. The composition of claim 1 wherein said branched complex carbohydrate is selected from the group consisting of carboxymethylcellulose and chitosan.

7. The composition of claim 1 further comprising a linear carbohydrate.

8. The composition of claim 1 wherein said cross-linking agent is a metallo-organic cross-linking agent which includes a multivalent metal ion.

9. The composition of claim 8 wherein said multivalent metal ion is selected from the group consisting of aluminum ions, chromium ions, and other metal ions with a valence greater than 2.

10. The composition of claim 8 wherein said metallo-organic cross-linking agent also acts as said cross-linking agent.

11. The composition of claim 1 wherein said cross-linking agent is an organic cross-linking agent containing a metal having an effective valence of at least 3.

12. The composition of claim 2 wherein said fatty acid is selected from the group consisting of a lauric, palmitic, oleic, and stearic acids, said branched complex carbohydrate is selected from the group consisting of carboxymethylcellulose, chitosan, and mixtures thereof, and said cross-linking agent is selected from the group consisting of aluminum acetate, aluminum borate, benzoate-based aluminum metallo-organic complex, palmitate-based aluminum metallo-organic complex, and mixtures thereof.

13. A composition of matter which acts as a synthetic sponge when allowed to hydrate comprising a non-hydrated mixture of:

undecylenic acid; and
   a branched complex carbohydrate;
   whereby said composition can be hydrated and cross-linked simultaneously in the presence of a hydrating solution.

14. The composition of claim 1 wherein said carboxylic acid comprises benzoic acid.

* * * * *